Figure 1A:
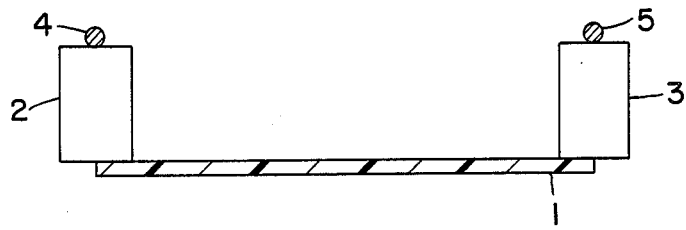

United States Patent [19]

Stålberg

[11] Patent Number: 4,874,491
[45] Date of Patent: Oct. 17, 1989

[54] METHOD OF SUPPLYING BUFFER SOLUTIONS TO ELECTROPHORETIC SEPARATION PROCEDURES

[75] Inventor: Ralph I. Stålberg, Uppsala, Sweden

[73] Assignee: Pharmacia AB, Uppsala, Sweden

[21] Appl. No.: 103,040

[22] PCT Filed: Feb. 9, 1987

[86] PCT No.: PCT/SE87/00057
§ 371 Date: Sep. 14, 1987
§ 102(e) Date: Sep. 14, 1987

[87] PCT Pub. No.: WO87/04948
PCT Pub. Date: Aug. 27, 1987

[30] Foreign Application Priority Data

Feb. 13, 1986 [SE] Sweden .................... 8600628

[51] Int. Cl.$^4$ .............................................. B01K 5/00
[52] U.S. Cl. .................................................. 204/182.8
[58] Field of Search ....................................... 204/182.8

[56] References Cited

U.S. PATENT DOCUMENTS

| | | | |
|---|---|---|---|
| 3,062,731 | 11/1962 | Durrum | 204/180.1 |
| 3,715,295 | 2/1973 | Tocci | 204/180 G |
| 4,006,069 | 2/1977 | Hiratsuka | 204/180 G |

OTHER PUBLICATIONS

Andrews, Electrophoresis: Theory, Techniques, and Biochemical and Clinical Applications, 2nd ed., p. 148 (1986).

Primary Examiner—John F. Niebling
Assistant Examiner—Isabelle Rodriguez
Attorney, Agent, or Firm—Fred Philpitt

[57] ABSTRACT

The process is one concerned with the field of electrophoresis and relates more particularly to a method of supplying the electrode buffer solutions by means of using buffer-containing gels as buffer reservoirs, thus making it unnecessary for the electrophoresis equipment to have special vessels for the buffers, and providing the possibility of using electrode buffer solutions of concentrations which are extremely high in electrophoresis contexts.

4 Claims, 1 Drawing Sheet

METHOD OF SUPPLYING BUFFER SOLUTIONS TO ELECTROPHORETIC SEPARATION PROCEDURES

The present invention is concerned with the field of electrophoresis and relates more particularly to a method of supplying buffer solutions to electrophoretic separation procedures by means of using buffer-containing gels as buffer reservoirs, thus eliminating the need for special buffer vessels in equipments employed for electrophoresis.

Electrophoretic separation is often carried out in a stabilizing matrix such as e.g. an agarose or polyacrylamide gel. The matrix is usually placed on a support in the form of for instance a disc of plastics, whereupon two opposite sides of the matrix are connected to one electrode buffer each. In case the matrix is enclosed within a cassette of for instance glass or plastics the contact is nevertheless made feasible due to the cassette being open at two opposite sides. The electrodes may be inserted in vessels containing the electrode buffers, and the connection to the matrix is established by means of some type of liquid bridge, for example a strip of paper or some other material capable of becoming soaked with buffer.

When electrophoretic separation is carried out in systems of this type a sample volume is deposited on the gel matrix, and then an electric field is applied between the electrodes whereby charged components of the sample are caused to migrate in the gel matrix. Experimental conditions may vary to a great extent—e.g. as regards the choice of gel matrix, pore size to thus permit separation also with respect to molecule size or particle size, or as regards regulation of pH and correspondingly regulation of the charges on the sample components. A feature common to all of these techniques is that the migration of the components in the gel matrix proceeds in an electrolytic medium.

With respect to the anodic buffers and cathodic buffers employed, an important requirement is that they must have a high buffering capacity; that is, they must not undergo any substantial change during the electrophoretic procedure, in spite of the reactions occurring at each of the electrodes. The most significant factors determining buffering capacity are the types of buffer components chosen, their concentrations, and the volume of the buffer solution.

As mentioned above electrophoresis is conventionally carried out with an equipment comprising special buffer tanks each of which is filled with the desired volume of its respective buffer. However, in the cases of some applications it is difficult to employ solutions of high concentration, because of liquid flow arising due to capillary forces at for instance the edges of the gel matrix. By means of maintaining a low electrode buffer concentration it is possible to avoid such faultiness or downright short-circuiting in the electric field of the separation gel as might otherwise be caused by the said type of liquid flow. A low electrode buffer concentration may be compensated for by increasing the buffer volume, although this of course necessitates incorporation of sufficiently large buffer vessels in the electrophoretic equipment. The potential drop outside the separation matrix could however in such cases be considerable. Especially in systems working with comparatively small gel matrices, for example in more or less automated systems, handling of the buffer solutions involves practical problems; it is desirable, therefore, that one should be able to reduce handling of liquid volumes to the greatest possible extent.

U.S. Pat. No. 3,715,295 has identified this problem and suggests mixing the buffer with a substance by means of which the buffer is obtained in a "semisolid" form. According to a preferred embodiment the buffer is incorporated in silica particles, whereupon a semisolid substance is added. Irrespective of the type of "semisolid" form chosen, a suitable volume thereof is transferred to a well at each end of the supporting baseplate of the electrophoretic equipment; thereafter the separation gel is positioned on the plate so as to establish direct liquid contact between the separation gel and the buffer. It should be noted that the equipment in this case too requires extra containers for buffer as mentioned above. The main difference from the normal procedure is that the buffer does not consist of a solution. A circumstance worth noting is that this method has not been used to any major extent despite the fact that the patent was published as early as 1973.

In SE7109110-2 (Millipore Corp.) an apparatus for electrophoresis is described, which has a special designed container for the gel material. At both ends the container has a depression forming the reservoirs for the cathode and the anode, respectively. The middle section has a depth corresponding to the thickness of the separation medium to be used. Before use a suitable amount of a water-containing gelforming solution is poured into the container and allowed to gel and a homogeneous gel piece with a thin middle section, the separation area, is formed. The electrolytic medium that is required for the separation is present during the gel formation and is accordingly homogeneously distributed in the gel. It is therefore not possible to obtain a higher concentration of electrolyte in those parts of the gel which constitute the electrode buffer reservoirs. Different buffer solutions in the two electrode buffer reservoires cannot be supplied this way and the same problem arises if a special separation buffer is desired. Since only homogeneous gels are formed by this technique such applications as gradient gel electrophoresis and other techniques requiring inhomogeneous gels are not easily carried out. The use of the apparatus described in SE7109110-2 is therefore limited to a few specific techniques in immunoelectrophoresis.

We have now found that a much simpler process is obtained if the buffer substance is incorporated in a gel material which is placed in contact with the separation matrix at each respective end thereof, whereupon conventional type electrodes are connected to the buffer gels. The process is particularly advantageous in horizontal electrophoresis procedures, in as much as the novel technique permits a buffer reservoir in the form of a piece of gel to be brought in contact with the separation matrix at each end or simply put on top of very thin matrices. Next the sample is deposited on the separation gel; and upon application of the electric field the sample components will migrate in the field within the separation gel region delimited by the two buffer gels. Similarly the buffer gels may be employed also in other types of electrophoresis operations by being contacted with opposite ends of the matrix.

One of the advantages inherent in the technique proposed according to this invention is that the electrophoretic equipment need not contain any vessels for liquid or semisolid electrode buffer. In this manner the equipment is simplified, and moreover the buffer gels employed in carrying out the invention are extremely easy to handle due to the fact that they have good mechanical strength properties. Since the electrode buffer is embedded in "solid" gel there will be no liquid transport caused by capillary forces. For this reason it now becomes possible to use much higher concentrations of electrode buffer than those that would be possible otherwise, and consequently buffer volumes can be kept low. Another advantage of "solid" gel buffer is that products of the electrode rections are prevented from reaching the separation gel where they conceivably might affect the result obtained. Electrode reactions give rise to changes in the buffer composition near the electrode surface, these changes extending increasingly further away from the electrode surface during the course of the electrophoresis procedure. FIG. 1 illustrates this phenomenon during an electrophoretic separation.

Figure 1B:
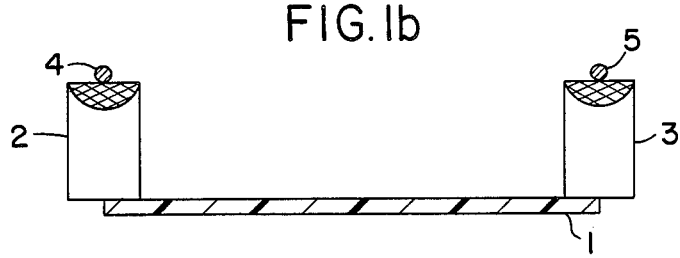
Figure 1C:
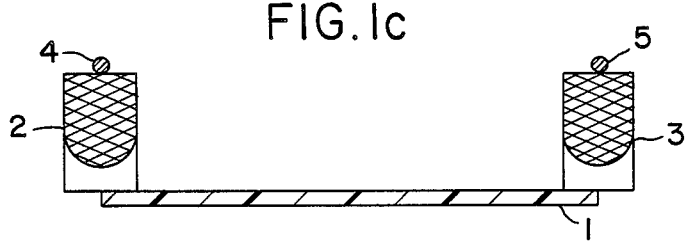

(1) is the separation matrix in the form of a gel plate. The two gels (2) and (3) which contain electrode buffer are placed in contact with the separation matrix at two opposite ends thereof. The two electrodes (4) and (5) are in direct contact with buffer gels (2) and (3) respectively. Electrophoretic separation starts when an electric field is applied between the electrodes; the change (hatched area) in the composition of the electrode buffers, such as it is produced by the electrode reactions, is illustrated in FIGS. 1(a) to (c) showing the conditions prevailing at zero, 25 and 100% respectively of the total period of electrophoresis.

The gel material to be used as the stabilizer for the electrode buffer is selected from the large group of known per se polymers which are water-insoluble at least at room temperature and have to fulfil the condition that their own charge is low. This is a necessary prerequisite for avoiding that the gel matrix will assume the role of a so-called electroendosmotic pump. Examples of suitable materials are of course the agarose grades developed specially for electrophoretic uses and fulfilling the aforesaid condition—such as e.g. Agarose IEF (Pharmacia AB, Uppsala, Sweden). The concentration of agarose in the composition consisting of buffer-containing aqueous gel will suitably be within the range of 1–4% by weight, preferably about 2%. Other materials that may obviously be employed are polyacrylamides of about 10% concentration and 2–7% degree of crosslinking.

The buffers which are incorporated in the gel material are of such types as are normally employed in electrophoretic separation procedures. Examples of such solutions are e.g. a mixture of trishydroxymethyl aminomethane (TRIS), glycine and hydrochloric acid; alanine, acetic acid; and various sodium phosphates, optionally with an addition of sodium dodecyl sulfate (SDS). Suitable concentrations of the aforesaid materials as well as further examples are set forth in Polyacrylamide Gel Electrophoresis, Laboratory Techniques (Pharmacia AB, Uppsala, Sweden). The amount of electrode buffer contained in each gel piece is usually within the range of from 80 to 99% by weight.

An upper limit for the concentration of buffer components in the gel material is set by the saturation limits for these components in aqueous solutions, and also by the risk of undesirable reactions occurring in certain cases, like for instance salting-out of the gel matrix. This will be the case with agarose if the concentration of buffer salts is high. A lower limit for the concentration of buffer components in the gel material may be determined by methodological studies, for example pH measurements in the buffer which will indicate the stage in which the buffering capacity of the buffer becomes insufficient. By way of ordinary trial routines a person skilled in the art will be able to find these limits in each individual case for various combinations of gel materials and buffer components.

When the buffer-containing gels are prepared, buffer solution is mixed with gel material under conditions such that the composition will easily form a homogeneous mix, e.g. at an elevated temperature; in the case of agarose a temperature of about 100° C. will be suitable. Alternatively buffer solution and monomer are mixed together, whereupon a polymerization reaction is initiated. In the case of polyacrylamide gel—one of the gels most commonly employed in electrophoresis—this may be accomplished in that acrylamide and bisacrylamide monomers are mixed with the buffer solution and then, after addition of an initiator substance, the mixture is made to polymerize. Other alternative well-known monomers may of course be incorporated in the reaction mixture.

Some very obvious advantages with the new technique are that any separation matrix and separation buffer can be used in combination with the desired electrode buffers, which are applied to the gel via the electrode buffer gels. Handling of electrode buffer solutions is avoided in the apparatus and very small electrode buffer gels can be used since high concentration of buffer in the gel is easily obtained. The buffer capacity is accordingly high and separations consuming many volt-hours can be carried out in an electrical field that is very little effected by time dependent changes in the electrode buffers.

The invention will now be illustrated by means of some non-limitative examples.

EXAMPLE 1

A buffer solution for native gradient gel electrophoresis was prepared in that 15 g of trishydroxymethyl aminomethane (TRIS) and 65 g of alanine were dissolved in 500 ml of water. 10 g of agarose were added, and the buffer was boiled with stirring until the agarose had dissolved. The solution was filled into 40×10×6 mm molds and permitted to cool. The gel buffer upon having solidified is suitable, with these dimensions, for being applied to separation gels having the approximate dimensions of 40×40×0.3 mm, containing for example an 0.026M TRIS, 0.033M acetic acid buffer.

EXAMPLE 2

A buffer solution for SDS gradient gel electrophoresis was prepared in that 12.1 g of trishydroxymethyl aminomethane (TRIS), 17.9 g of tricine and 2.8 g of sodium dodecyl sulfate (SDS) were dissolved in 500 ml of water. 10 g of agarose were added, and the buffer was boiled with stirring until the agarose had dissolved. The solution was filled into 40×10×6 mm molds and permitted to cool. Thus cooled the gel buffer is suitable for being applied to separation gels dimensioned as set forth above.

I claim:

1. In the known electrophoretic separation process that involves depositing a sample volume on a gel matrix that is in contact with two electrodes and a buffer substance, then applying an electric field between two electrodes whereby charged components of the sample are caused to migrate in the gel matrix, the improvement comprising that said buffer substance is incorporated in a gel material so as to form a solid buffer gel that has good mechanical strength properties such that a supporting vessel is not required, said gel material being selected from the group consisting of agarose and a polyacrylamide.

2. A process according to claim 1 wherein the gel material is agarose and comprises 1–4% by weight of the buffered gel.

3. A process according to claim 1 wherein the gel material is agarose which comprises 2% by weight of the buffered gel.

4. A process according to claim 1 wherein the gel material is a polyacrylamide of about 10% concentration and 2–7% degree of cross-linking.

* * * * *